(12) United States Patent
Wachtel et al.

(10) Patent No.: US 8,950,396 B2
(45) Date of Patent: Feb. 10, 2015

(54) DISPENSING DEVICE (CAT)

(75) Inventors: Herbert Wachtel, Ingelheim am Rhein (DE); Frank Richter, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1555 days.

(21) Appl. No.: 12/236,846

(22) Filed: Sep. 24, 2008

(65) Prior Publication Data

US 2009/0139517 A1   Jun. 4, 2009

(30) Foreign Application Priority Data

Sep. 25, 2007  (EP) .................................... 07018787

(51) Int. Cl.
*A61M 15/00* (2006.01)
*A61M 11/02* (2006.01)
*A61M 16/10* (2006.01)

(52) U.S. Cl.
CPC ....... *A61M 15/0028* (2013.01); *A61M 15/0045* (2013.01); *A61M 15/0026* (2013.01); *A61M 15/0035* (2013.01); *A61M 15/0048* (2013.01); *A61M 15/0061* (2013.01); *A61M 2202/064* (2013.01); *A61M 2205/8218* (2013.01); *A61M 2206/16* (2013.01)
USPC ............ 128/203.15; 128/203.21; 128/203.28; 128/200.22

(58) Field of Classification Search
CPC ..... A61M 11/00; A61M 11/02; A61M 13/00; A61M 15/00; A61M 15/001; A61M 15/0028; A61M 15/0031; A61M 15/0036; A61M 15/0041; A61M 15/0045; A61M 15/0048; A61M 15/0091

USPC ............ 128/200.14–200.23, 203.12, 203.15, 128/203.21, 203.28; 222/630–635; 604/58
See application file for complete search history.

(56) References Cited

U.S. PATENT DOCUMENTS

| | | | |
|---|---|---|---|
| 4,627,432 A | 12/1986 | Newell et al. | |
| 6,014,969 A * | 1/2000 | Lloyd et al. ............. | 128/200.14 |
| 6,158,676 A | 12/2000 | Hughes | |
| 6,880,555 B1 * | 4/2005 | Brunnberg et al. ...... | 128/203.12 |
| 2003/0183230 A1 * | 10/2003 | Nelson et al. ............ | 128/203.15 |
| 2003/0205229 A1 * | 11/2003 | Crockford et al. ....... | 128/204.23 |
| 2005/0087189 A1 | 4/2005 | Crockford et al. | |
| 2005/0121023 A1 * | 6/2005 | Braithwaite ............ | 128/200.14 |
| 2006/0260606 A1 * | 11/2006 | Coifman .................. | 128/200.14 |
| 2008/0156319 A1 * | 7/2008 | Avni ........................ | 128/200.14 |
| 2009/0293874 A1 * | 12/2009 | Braithwaite ............. | 128/203.15 |

FOREIGN PATENT DOCUMENTS

| | | |
|---|---|---|
| EP | 1 795 221 A1 | 6/2007 |
| WO | 2006/002654 A1 | 1/2006 |
| WO | 2006/037636 A1 | 4/2006 |
| WO | 2007/062721 A1 | 6/2007 |

* cited by examiner

*Primary Examiner* — Valerie L Skorupa
(74) *Attorney, Agent, or Firm* — Roberts Mlotkowski Safran & Cole, P.C.; David S. Safran

(57) ABSTRACT

A dispensing device, a storage device and a method are proposed for dispensing a formulation as a spray. The formulation is dispensed by means of a gas stream. To improve the dispensing effect, pressure pulses are generated in the gas stream and/or the direction of gas flow alternates. The formulation is dispensed through a duct. The duct is connected to a storage chamber containing the formulation via a sharp edge or transition portion.

7 Claims, 8 Drawing Sheets

DISPENSING DEVICE (CAT)

BACKGROUND OF THE INVENTION

1. Field of Invention

Figure 1:
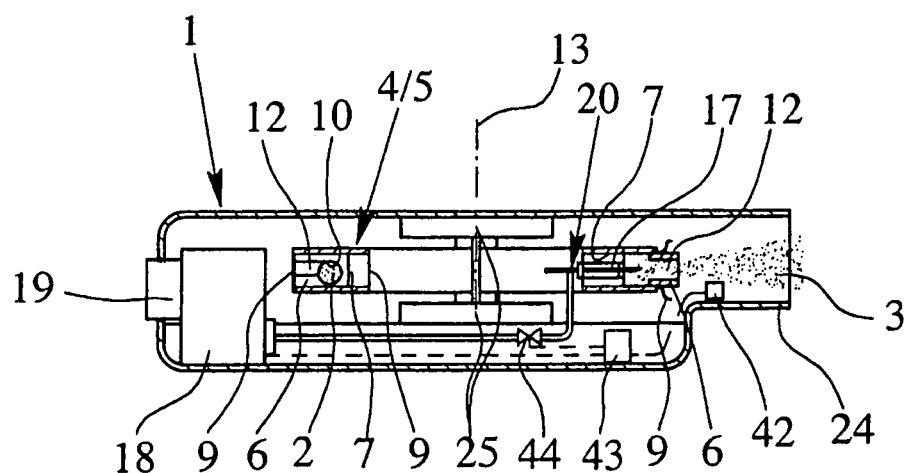

The present invention relates to a dispensing device for dispensing a preferably medical formulation, in particular containing or consisting of a drug or mixture of drugs as a spray, to a storage device for a preferably medical formulation, in particular, containing or consisting of a drug or mixture of drugs, and to a method for dispensing such a formulation as a spray.

2. Description of Related Art

Drugs delivered through dispensing devices, in particular inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles or droplets. As currently believed to be understood, particles having an aerodynamic diameter of less than 2 micrometer are considered to be potentially optimal for deposition in the alveolar region of the lung. Particles that have an aerodynamic diameter of between 2 and approximately 5 micrometer may be more suitable for delivery to the bronchiole or bronchi regions. Particles with an aerodynamic size range greater than 6 micrometer, and more preferably 10 micrometer, are typically suitable for delivery to the laryngeal region, throat or nasal passages.

In most cases, it is desired to achieve a high inhalable fraction and a high delivery efficiency, i.e., the fraction of the initial dose of drug that reaches the desired region, in particular, in the lung. This depends on various factors, in particular, on the characteristics of the generated spray plume, such as the propagation velocity of the plume, particle size and its distribution, fraction of small particles, fraction of gas or the like. In the present invention, the desired sprayed plume characteristics include preferably a small particle size, a high fraction of the drug particles with the diameter of 6 micrometer or less, a low propagation velocity and/or a long duration of spray generation and possible inhalation.

U.S. Pat. No. 4,627,432 discloses a device for administering medicaments to patients, namely an inhaler. The inhaler comprises a disk-like blister pack having a plurality of blister pockets arranged in a circle. Each blister pocket contains a dose of the powder. A plunger can open a blister pocket. When a blister is opened, the medicament can be withdrawn by a patient inhaling through a mouthpiece.

International Patent Application Publication WO 2005/002654 A2 discloses a passive device for dispensing individual doses of powder. The doses are contained in respective pockets of a disc-shaped carrier and opened by outwardly rupturing a covering foil in axial direction by means of pressure on an opposite side surface. The pockets are moveable in axial direction into an airstream generated by breathing of a patient for dispensing a dose of powder from the pocket. The device provides individual respective deaggregation flow paths for each pocket, split airstreams allowing improved entrainment of powder, a cam mechanism for outwardly rupturing the pockets, an indexing mechanism linked to the cam mechanism, and a dose counter.

It is difficult to empty the respective pocket completely during a dispensing operation. Incomplete emptying results in decreased delivery efficiency. Some powder may be lost in the inhaler and not dispensed because the known solutions require relatively long paths for the powder until the powder reaches a nozzle and is actually dispensed. This might reduce the delivery efficiency further. In addition, de-agglomeration of the powder is difficult.

International Patent Application Publication WO 2006/037636 A2 and the corresponding U.S. Patent Application Publication 2007/272763 disclose an active dispensing device with an air pump for dispensing powder individually from storage chambers in a common carrier. Preferably, an individual deaggregation and outlet duct having a flat cross-section is associated to each storage chamber.

International Patent Application Publication WO 2007/062721 A1 and the corresponding U.S. Patent Application Publication 2007/163574 disclose an active dispensing device for dispensing a formulation as a spray. The dispensing device comprises a storage device with multiple pre-metered doses of the formulation in separate inserts. The dispensing device comprises a means for pressurizing gas, in particular, an air pump, for generating a gas stream flowing through the respective insert for dispensing a dose of the formulation.

In general, it is very difficult to empty storage chambers or the like when the formulation is dispensed by means of a gas stream. Further, de-agglomeration of the formulation is difficult. Therefore, there is a need to allow an optimized dispensing effect (better emptying of storage chambers or the like and/or better de-agglomeration) when the formulation is dispensed by means of a gas stream.

SUMMARY OF THE INVENTION

In accordance with the present invention, the desired spray plume characteristics preferably include a small particle size, a high fraction of drug particles with a diameter of 6 µm or less, a low propagation velocity and/or a long duration of spray generation and possible inhalation.

The present invention relates to the dispensing of a preferably medical formulation. The term "formulation" relates in particular to powder, but may include or relate to liquids as well. Consequently, the fine "particles" may be either solid or liquid. The term "liquid" has to be understood preferably in a broad sense covering inter alia solutions, suspensions, suslutions, mixtures thereof or the like. More particularly, the present invention relates to the dispensing of formulations for inhalation, such as medical formulations containing or consisting of at least one drug.

In the following, the description will focus mainly on powder formulations. However, the same applies for liquid formulations.

In particular, the present invention is concerned with dry powder inhalers for the delivery of drugs to the lungs. Many dry powder inhalers are on the market or have been proposed. There are two main types, namely the passive ones and the active ones. In passive inhalers all the energy required for de-agglomerating the powder and transferring the powder to the lungs is provided by the breathing of a user, respectively the patient. In active inhalers there is an additional source of energy to help to transfer and de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependent on the breathing of the patient. The transfer and de-agglomeration of the powder and hence the inhalable fraction is a function of the flow rate of inhaled air through the device and, therefore, varies greatly from patient to patient.

Dry powder inhalers are subdivided into single dose and multi-dose devices or inhalers. Multi-dose inhalers are further subdivided into pre-metered types where the doses are stored individually and into metering inhalers where each powder dose is metered in the device.

Multi dose pre-metered inhalers have the advantage that the single doses are metered under strict factory conditions and the powder can quite easily be isolated from the atmosphere. In many applications the active drug powder is mixed with a carrier such as lactose. The lactose and/or active drug (s) tend to absorb humidity from the atmosphere, which makes them stick together and difficult to transfer and de-agglomerate.

The present invention relates, in particular, to an active, gas (preferably air) powered, pre-metered multi-dose dispensing device for dispensing a formulation containing or consisting of a drug, such as a dry powder inhaler.

A primary object of the present invention is to provide an improved dispensing device, storage device and method for dispensing a preferably medical formulation, in particular wherein an optimized dispensing effect can be achieved to dispense a preferably powdered formulation by means of a gas stream.

The above object is achieved by a dispensing, by a storage device and by a method as described herein.

According to a first aspect of the present invention, pressure pulses are generated in the gas stream during dispensing of one dose. Alternatively or additionally, the direction of gas flow alternates during dispensing one dose of the formulation. Thus, a significantly improved dispensing effect can be achieved. In particular, the formulation may be entrained or loosened by the gas stream more effectively. Further, the formulation can be deagglomerated more effectively.

According to a second aspect of the present invention, the duct for dispensing the formulation, and in particular, generating the spray, is connected to its associated storage chamber containing the dose of the formulation to be dispensed via a sharp edge or sharp transition portion. Thus, a better dispensing effect can be achieved. In particular, a tapered transition portion is avoided between the large storage chamber and the small duct. This avoids clogging of the transition portion and, therefore, improves the dispensing effect of the gas stream.

Preferably, the gas stream is generated or enabled by a gas pressurizing means, i.e., preferably, the dispensing device is an active inhaler or the like.

According to an alternative embodiment, however, the gas stream may also be generated by breathing in by a user or patient. Then, the dispensing device is, in particular, a passive inhaler.

Preferably, receptacles or cavities of the storage device respectively comprise a moveable insert as storage member with the respective dose of formulation. Preferably, each insert comprises a duct in order to directly form the spray during use. Thus, the spray is generated by the respective insert when pressurized gas is supplied. This makes it possible to respectively generate sprays with the desired spray plume characteristics with high accuracy.

Further aspects, advantages and features of the present invention will be apparent from the following detailed description of preferred embodiments in conjunction with the accompanying drawings.

BRIEF DESCRIPTION OF THE DRAWINGS

FIG. 1 is a schematic sectional view of a dispensing device with a storage device according to an embodiment during dispensing;

FIG. 2 is a schematic sectional view of the storage device with an insert;

FIG. 3 is a schematic sectional view of the insert;

FIG. 4 is another schematic sectional view of the storage device with pierced insert;

FIG. 5*a* is a schematic view of the dispensing device;

FIG. 5*b* is a graph of the pressure over time;

FIG. 5*c* is a graph of the stroke of a pump part over time;

FIG. 6 is a schematic view of another dispensing device;

FIG. 7 is a schematic view of a dispensing device according to another embodiment;

FIG. 8 is a schematic view of inner components of the dispensing device according to FIG. 7 with the air assembly retracted;

FIG. 9 is a schematic view of inner components of the dispensing device according to FIG. 7 with the air assembly advanced in an activated state; and FIG. 10 is a schematic view of inner components of the dispensing device according to FIG. 7 with the air assembly advanced after dispensing.

DETAILED DESCRIPTION OF THE INVENTION

In the figures, the same reference signs are used for the same or similar parts and components, wherein, preferably, the same or similar features, aspects and/or advantages are achieved in the different embodiments, even if a repetition of the respective description is omitted.

FIG. 1 shows in a schematic sectional view—for illustration purposes and not to scale—a dispensing device 1 according to the present invention. The dispensing device 1 is preferably an active device, in particular, gas powered. Preferably, the dispensing device 1 is a preferably oral or nasal inhaler, in particular, a dry powder inhaler, for a user, respectively a patient (not shown).

Preferably, the dispensing device 1 is portable and/or handheld.

The dispensing device 1 may be used for dispensing any formulation 2 as defined in the introductory part of the description. In particular, a medical formulation 2 for inhalation will be used. The formulation 2 preferably contains or consists of at least one drug. When the formulation 2 is dispensed, a spray 3 is generated as indicated in FIG. 1. The spray 3 includes or consists of fine particles (solid and/or liquid), and preferably, has the desired spray plume characteristics.

The formulation 2 may be a liquid, in particular, a solution, a suspension or any mixture thereof, i.e., a so-called suslution. Preferably, when different drugs are dispensed simultaneously, a suslution may be used. The principle of the suslution is based on that different drugs may be combined in one formulation simultaneously as a solution and as a suspension. In this respect, reference is made to European Patent Application Publication EP 1087 750 A1 and corresponding U.S. Pat. No. 6,423,298, which are hereby incorporated herein by reference in this respect.

Preferably, the formulation 2 is a powder. The powder may be a pure drug or a mixture of at least two drugs or any other mixture of at least one drug. In addition, the powder may contain at least one other material, in particular, a drug carrier, such as lactose. In the following, the description focuses on powder as formulation 2. However, this applies in a similar manner if a liquid formulation 2 is used.

Preferably, the mean diameter of the powder particles is about 2 to 7 μm, in particular, 6 μm or less. This applies in particular if the powder does not contain any drug carrier, such as lactose.

If the powder contains a drug carrier, such as lactose, and at least one drug, the powder 2 may have a particle size of 20 to 300 µm, in particular, about 30 to 60 µm. However, the de-agglomeration, which will be described later in more detail, may result even in this case in a spray 3 with a smaller particle size, e.g., of about 10 µm or less. In particular, the drug may be separated from the drug carrier during de-agglomeration so that primarily the drug will be inhaled due to its small particle size of about 2 to 6 µm and the larger drug carrier will be swallowed when using the dispensing device as an inhaler. Alternatively or additionally, breaking or opening of the drug carrier is possible during de-agglomeration.

The diameters mentioned above and below may be understood as mass medium aerodynamic diameters and/or may apply to the particle size or a fraction of the particles of the spray 3.

Preferably, the formulation 2 is pre-metered in separate or individual doses, which can be discharged one after the other by the dispensing device 1, in particular, for inhalation.

The dispensing device 1 is adapted to receive or comprises a storage device 4 for storing preferably multiple and pre-metered doses of the formulation 2. The storage device 4 may be integrated into the dispensing device 1 or form part of the dispensing device 1. Alternatively, the storage device 4 may be a separate part that can be inserted or connected with the dispensing device 1 and optionally replaced.

Figure 2:
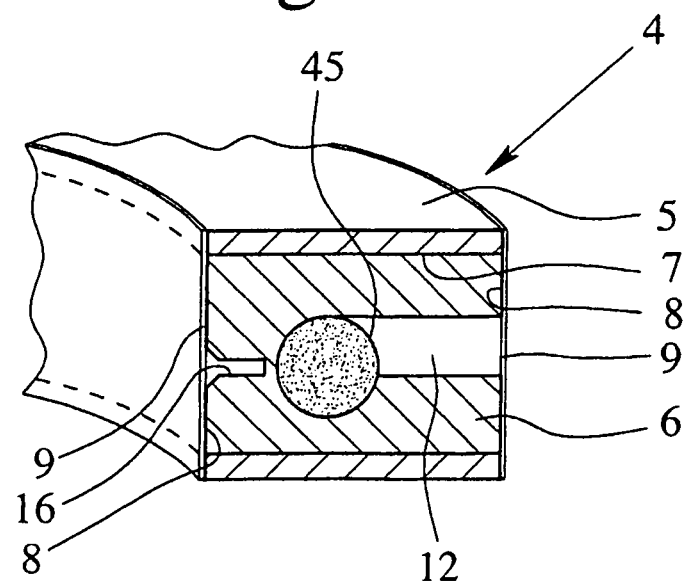

FIG. 2 shows a schematic cross-section of the preferably ring-like storage device 4.

The storage device 4 preferably comprises a carrier 5 and at least one storage member, preferably multiple storage members. Preferably, the storage members are inserts 6. Therefore, the word "insert" is used in the following.

In particular, the carrier 5 may comprise or support 20 to 100, preferably 30 to 60 inserts 6. Each insert 6 contains preferably one pre-metered dose of the formulation 2. However, each insert 6 may also contain more than one formulation 2, i.e., different formulations 2. Additionally or alternatively, different inserts 6 may contain different formulations. In the present invention, "different" means in particular that the formulations 2 differ in at least one of the composition, the drug, the dose or amount, the concentration, and consistence of the formulation 2, e.g., liquid or dry powder.

The storage device 4 or carrier 5 preferably comprises multiple cavities 7 or receptacles for receiving or with the inserts 6. In particular, each insert 6 is located in a separate cavity 7. Preferably, the cavities 7 are separate from each other, and in particular, sealed relative to each other.

In the present embodiment, each cavity 7 comprises at least one opening 8, in particular, two preferably opposed openings 8 (here, at the radially inner and outer circumference or periphery).

The cavities 7 or its openings 8 are covered by respective covers or seals 9 which are preferably formed by, preferably, heat-sealed foils on opposite sides of the respective cavity 7 or the carrier 5. In the present embodiment, the seal 9 is, in particular, a metallic foil, such as aluminum foil, plastic foil, a multi-layer arrangement or the like. The seal 9 preferably protects the inserts 6 and/or formulation 2 against humidity, dirt, moisture and/or the like. The seals 9 are respectively resistant and/or impermeable, in particular, gas-tight.

In this preferred embodiment, the storage device 4 or carrier 5 is ring-like and the cavities 7 extend at least substantially in radial direction. The cavities 7 are distributed around the perimeter of or along the storage device 4 or carrier 5, preferably equally spaced with respect to the adjacent cavities 7.

In the present embodiment, the storage device 4/carrier 5 is preferably rotatable around axis 13 shown in FIG. 1. In particular, the dispensing device 1 can be opened and the storage device 4/carrier 5 can be inserted or replaced.

The carrier 5 may be a molded element, a ring, a stripe, a cartridge, a blister or a container. Preferably, the storage device 4 or carrier 5 is rigid or at least essentially stiff.

Preferably, the carrier 5 is made of foil, plastics, ceramics and/or composite material, in particular, of thermoplastics or thermoplastic elastomers.

Each cavity 7 or receptacle preferably forms a guide for the associated insert 6, in particular so that the insert 6 is moveable in at least or only one direction and/or at least or only partially out of the cavity 7 or receptacle.

FIG. 1 shows a situation, where the insert 6 on the right side has already been pushed partially out of its associated cavity 7 and/or the outer opening 8 and/or through the respective seal 9 of its associated cavity 7 for opening the seal 9. The insert 6 shown on the left side of FIG. 1 is still within its closed and sealed cavity 7.

Each insert 6 is preferably produced filled with the respective dose of formulation 2 separately from the storage device 4 or carrier 5 and, then, inserted into its respective cavity 7 or receptacle.

Preferably, each insert 6 is molded and/or made of foil, plastics, ceramics and/or composite material, in particular of thermoplastics or thermoplastic elastomers and for seals of elastomers or silicone.

According to a preferred embodiment, the carrier 5 and/or the inserts 6 are made of at least one of the following materials or any mixture or blend thereof:

ABS (acrylonitril-butadiene-styrene copolymer); SAN (styrene-acrylonitril-copolymer); PBT (polybutylene terephthalate); PC (polycarbonate); CA (cellulosic acetate); EVA (ethylene vinylacetate copolymer); PA (polyamide); PE (polyethylene); PP (polypropylene); PMMA (polymethyl-methacrylate); POM (polyoxymethylene, polyacetal); PPS (polyphenylene sulfide); PS (polystyrene); PBTP (polybutylene terephthalate); TPU (thermoplastic polyurethane); blend of PC and PBTP; blend of PC and ABS; LCP (liquid crystal polymers); PHCS (polypyrrolor polythiophene); PPA (polyphthalamide); PSU (polysulfone); PTFE (polytetrafluorethylene); PUR (polyurethane); SB (styrene-butadiene copolymer); PIB (polyisobutylene); PAN (peroxyacylInitrate); PET (polyethylene terephthalate); AMMA (acrylonitril-methymethacrylat copolymer); PAR (polyarylate); PEEK (polyetheretherketone); COC (cycloolefine copolymer).

Each insert 6 may form a preferably block-like unit and/or be rigid. Alternatively, the inserts 6 may be flexible. In particular, each insert 6 may be a unitary unit or made of multiple elements. In particular, the insert 6 forms one component or is made of one piece. Each insert 6 may be a molded element, a cartridge, a blister, a capsule, a container or the like.

In the following, a preferred construction of one insert 6 is explained. Preferably, all inserts 6 are identical. However, it is also possible that all or some inserts 6 are different. For example, two or more groups of different inserts 6 can be provided. It is possible that one group has a different dose or different formulation 2 than the other group. For example, the inserts 6 of the different groups could be arranged alternately one after the other so that a patient or user may use, for example, each morning an insert 6 of one group and each evening an insert 6 of the other group.

Figure 3:
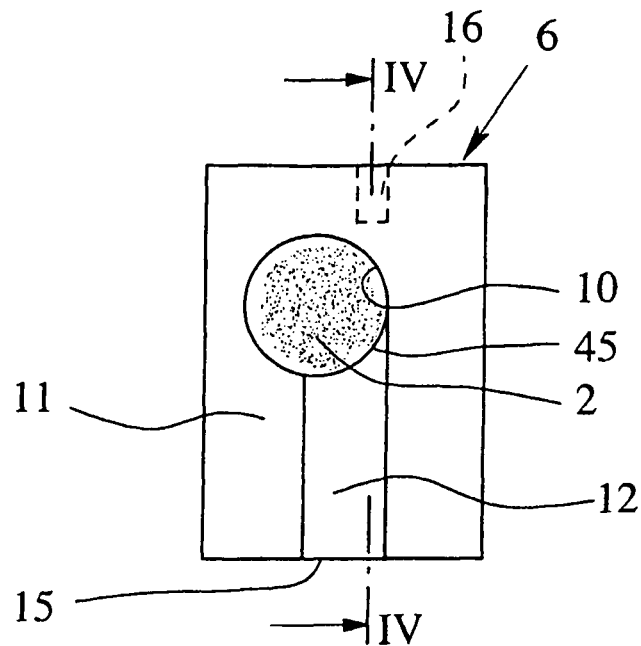
Figure 4:
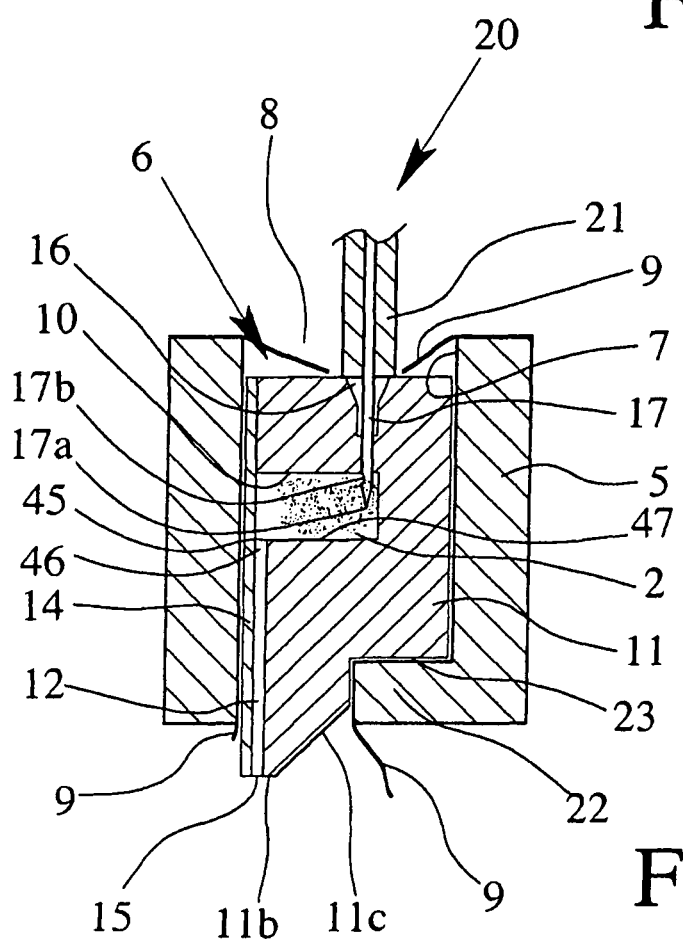

Each insert 6 preferably comprises a storage chamber 10 for a single dose of the formulation 2. The schematic sectional views according to FIGS. 2 & 3 show a preferred embodiment of the insert 6. The schematic sectional view according to FIG. 4 is taken along line IV-IV of FIG. 3 and shows the insert 6 when the insert 6 has been pushed out from the carrier 5 and opened/pierced.

The insert 6 comprises a storage chamber 10 for the formulation 2. In the present embodiment, the storage chamber 10 is preferably formed in a molded base member 11 of the insert 6.

The insert 6/base member 11 further comprises a duct 12 or the like for deagglomerating and/or discharging the formulation 2 during the dispensing operation. The formulation 2 is dispensed through the duct 12 during the dispensing operation, in particular for directly forming the spray 3.

Preferably, the duct 12 is flat and/or rectangular in cross section. In particular, the cross section corresponds to a hydraulic diameter of less than 1 mm. In particular, the duct 12 is designed as described in International Patent Application Publication WO 2006/037636 A2 and corresponding U.S. Patent Application Publication 2007/272763, which are hereby incorporated by reference.

According to another embodiment (not shown), the duct 12 can also be used as a reservoir (storage chamber 10) for the formulation 2. In this case, the separate storage chamber 10 is not required. Then, the duct 12 is designed to enable sufficient mixing of the gas with the formulation 2 and sufficient de-agglomeration of the powder formulation 2.

Preferably, the spray 3 having its desired spray characteristics is directly ejected or discharged from the insert 6/duct 12 or is generated by the duct 12 only.

In particular, the insert 6 forms one component or is made of one piece.

The insert 6 or duct 12 can comprise or form a nozzle arrangement, preferably, at an outlet 15 or end of duct 12 or formed by duct 12.

Preferably, the storage chamber 10 and/or the duct 12 is formed by or in the base member 11, in particular, by a recess, groove or the like in the base member 11 and by an associated cover member 14 as shown in FIG. 4. In particular, the duct 12 forms a channel from the storage chamber 10 to the outlet 15 of the insert 6, in particular, for directly discharging or dispensing the formulation 2 as spray 3 as shown in FIG. 1. Preferably, the base member 11 is molded and/or rigid. Preferably, the cover member 14 is rigid and/or rigidly fastened, e.g., welded, to the base member 11.

It is noted that the inserts 6 may be or are preferably open, i.e., not sealed, in particular, at their respective outlet 15 only. Experiments have shown that sealing of the carrier 5/cavity 7 is sufficient. The duct 12 is preferably so small in cross section or provided with a bursting element or any other suitable means that the formulation 2 is not discharged, preferably, even with seal 9 opened and/or during strong shaking of the dispensing device 1/storage device 4, but preferably, only when gas (air) is forced through the insert 6 and duct 12.

The inserts 6 and cavities 7 are preferably adapted to each other such that the seals 9 contact end faces of the inserts 6, and thus, cover the outlets 15. This may further prevent any formulation 2 from dissipating through the duct 12/outlet 15 before the desired dispensing. In order to increase the seal or cover effect produced by seal 9, the inserts 6 may be slightly longer than the cavities 7 and/or protrude at their outlet side and/or be pressed with their outlets 15 against the seals 9 or vice versa.

The insert 6 preferably comprises an inlet for supplying preferably pressurized gas into the storage chamber 10 to force the formulation 2 through the duct 12 and to directly generate the described spray 3. In the present embodiment, the inlet is preferably formed by a weak or thinned portion and/or designed as a preferably tube-like recess 16 or blind bore formed in the base member 11. Preferably, the recess 16 is not directly connected to the storage chamber 10, but is separated by a seal or an intermediate or thinned wall or the like. This wall can be penetrated, e.g., by a connecting element, preferably a piercing element 17, such as a needle, as shown schematically in FIG. 6, or by any other suitable opening, connecting and/or supply means, in particular, when the respective insert 6 is connected to a gas supply as explained in the following. Preferably, the piercing element 17 is a hollow needle, in particular, with a solid or closed tip 17a and a side opening 17b adjacent the tip 17a for supplying the pressurized air into the insert 6/storage chamber 10.

In the present invention, the expression "piercing element 17" preferably covers also all other suitable types of means for opening and/or connecting the storage device 4, the carrier 5, a cavity 7 and/or an insert 6 and/or for directly or indirectly supplying gas to an insert 6 or its respective storage chamber 10.

It is noted that the cross sections of the inserts 6 and the cavities 7 are preferably polygonal, in particular, rectangular or that other guiding means are preferably provided, in order to avoid that the inserts 6 may pivot within the cavities 7. However, if the inserts 6 are rotatably symmetrical with respect to the recess 16 or any other connection/inlet for gas supply and with respect to its outlet 15, the inserts 6 may also be cylindrical and/or can rotate within the cavities 7. This may facilitate insertion of the inserts 6 into the cavities 7 during production.

The duct 12 is preferably at least tangentially connected to the storage chamber 10 as shown in FIG. 3. Preferably, the duct 12 is connected at one axial end of the preferably cylindrical chamber 10, and the gas inlet (recess 16/piercing element 17) is connected or connectable to the other axial end of the chamber 10 as indicated in FIG. 4. In particular, the gas inlet is connected also tangentially to the storage chamber 10, such that swirls are generated when entering the gas with a swirl direction supporting discharge of the mixture of gas and formulation 2 through the duct 12, which connects tangentially to the rotational direction of the swirl.

Preferably, the duct 12 is connected to its associated storage chamber 10 via a sharp edge or transition portion 45 as shown in FIG. 4. In particular, the ducts 12 have an at least essentially constant cross section which preferably begins at an entry port or opening 46 of the duct 12 at an inner side wall 47 of the storage chamber 10.

In particular, the storage device 4 or storage member/insert 6 does not comprise a tapered transition portion 45 where the storage chamber 10 and the duct 12 are interconnected. Thus, clogging of the formulation 2—in particular, in this transition portion 45—can be avoided or at least minimized.

The transition portion 45 preferably has a constant cross section, forms the beginning of the duct 12, forms the entry opening 46 of the duct 12, and/or is not tapered.

Therefore, an improved dispensing effect can be achieved.

The dispensing device 1 uses preferably pressurized gas, in particular, air, to force the formulation 2 through the duct 12 to de-agglomerate the powder and/or to generate the spray 3 with fine powder particles. Preferably, the dispensing device 1 comprises a means for providing pressurized gas, in the present embodiment an air pump 18, as indicated in FIG. 1, which can preferably be actuated or operated manually, e.g., as indicated by handle or actuator 19 and/or by a spring means as shown later in another embodiment.

Figure 5A:
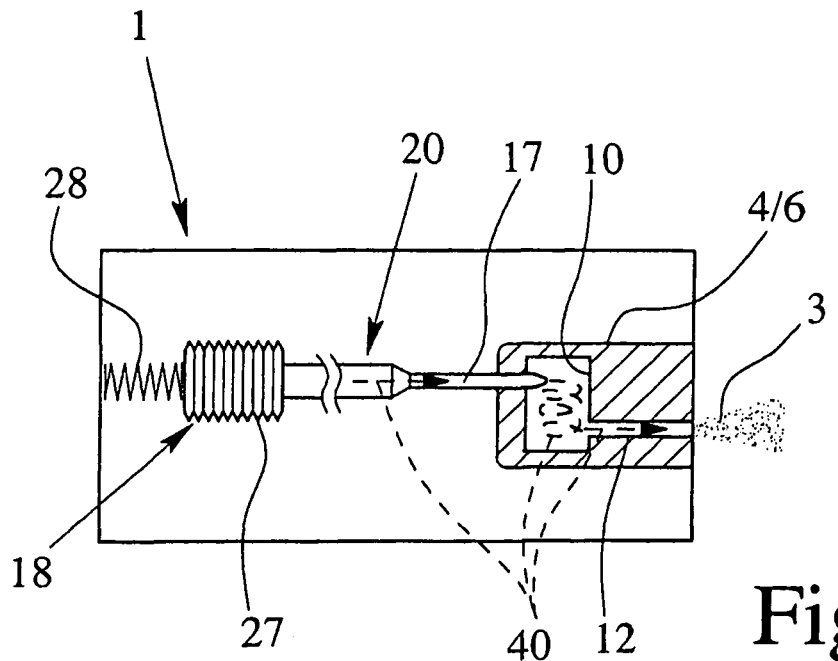

In particular, the air pump 18 comprises or is formed by a bellows 27 as schematically shown, e.g., in FIG. 5a. but, it could be also a piston-cylinder-arrangement. Instead of the air pump 18, the means for providing pressurized gas can be, e.g., a capsule, container or the like containing pressurized or liquefied gas for powering the dispensing device 1, i.e., dispensing the formulation 2 as desired. Therefore, the term "means for pressurizing gas" has to understood preferably in a broad sense to cover these and similar alternatives to the pump 18 as well.

The means for providing pressurized gas/air pump 18 may provide a gas pressure of less than 300 kPa, in particular, about 50 to 200 kPa. This is preferably sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular, the storage chamber 10 of the respective insert 6.

Preferably, all pressure values mentioned in the present description are gauge pressures, i.e., pressure differences. All pressure values relate to the pressure in a gas storage, such as a container with pressurized or liquefied gas, or provided by air pump 18 or relate to the pressures acting in the chamber 10 and/or in the duct 12.

FIGS. 1 & 5a show that the dispensing device 1 preferably comprises a mechanism 20 for individually opening the cavities 7, for individually moving the inserts 6, preferably radially (here outwardly) and/or through an associated opening 8 and/or seal 9, and/or for individually connecting the inserts 6 to the gas supply, in particular, to the air pump 18. The mechanism 20 preferably comprises the piercing element 17 and/or any other suitable connecting or actuation element.

In particular, in a first operation phase the piercing element 17 penetrates the seal 9 and, then, is inserted into the recess 16 and through the intermediate, end or weakened wall into the storage chamber 10 and, thus, connects the respective insert 6 to the gas supply. Before, simultaneously or afterwards, e.g., during the further movement, the mechanism 20 pushes the insert 6 through the other or outer opening 8 and through the respective seal 9 at least partially out of its cavity 7. Preferably, the mechanism 20 acts directly on the respective insert 6 to cause its movement. Here, the piercing element 17 is preferably provided with a shoulder or abutment or sleeve 21 (shown schematically in FIG. 6) that abuts against the insert 6 to positively produce the desired movement of the insert 6 when moving the mechanism 20/piercing element 17. The final situation is shown in FIG. 1 on the right side and in FIG. 6 with protruding insert 6.

It is noted that any other driving mechanism can be used to move the insert 6 to open one opening 8/one seal 9/the respective outlet 15 or the insert 6, itself. In particular, it is possible to realize the preferred pushing of the insert 6 through the seal 9 independently of the connecting or piercing of the insert 6.

In order to facilitate opening of the respective seal 9, the insert 6 comprises preferably an opening means, in particular, a tip portion 11b, and/or is tapered at its outlet end. In particular, the insert 6 or its base 11 comprises an inclined portion 11c—preferably, at least or only on one flat side of the insert 6 or base 11—so that the insert 6/base 11 is tapered towards the outlet 15, as shown schematically in FIGS. 4 & 6. Thus, it is possible to form a tip or tip portion 11b, which forms a front face with reduced or minimal surface. It is even possible to form a cutting edge at the outlet end.

Alternatively or additionally, it is possible to form or provide any other suitable cutting element as opening means at the insert 6, in particular, at its outlet end.

In particular, the stroke or outward movement of the insert 6 is adapted and preferably so long, such that the desired opening of the seal 6 is ensured, and in particular, that the broken, cut and/or rupture parts of the opened seal 9 cannot hinder or cover or interfere with the outlet 15 of the insert 6. In the present embodiment, the seal 9 substantially ruptures at one side of the opening 8 where the tip portion 11b of the insert 6 is located. The short rest of the seal 9 mounted on this side of the opening 8 cannot interfere with the outlet 15 of the protruding insert 6 because it is preferably shorter than the outward stroke of the insert 6. The longer part of the seal 9 connected to the other side of the opening 8 will be bent or pivoted away by the insert 6.

In the present embodiment, the opening and/or cutting of the seal 9 takes place at one side or adjacent to one edge of the preferably rectangular opening 8 when the respective insert 6 is moved outward of its cavity 7 for activating and later dispensing. The opening means, tip portion 11b, cutting element or the like is located at one side of the insert 6, and in particular, adjacent to one side of its cavity 7 and opening 8 so that the mentioned opening of the respective seal 9 occurs as described when the insert 6 is moved outward. With other words, the location of the opening or cutting means may be and, in particular, is used to ensure or cause a desired opening pattern and/or location of the respective seal, in particular at one side and/or adjacent to one edge of the opening 8. However, other opening locations can be chosen. For example, it is also possible to open the respective seal 9 in the center. Additionally or alternatively, the insert 6 may be adapted—in particular, by provision of two or more opening or cutting means—to open or rupture or cut the respective seal 9 at multiple regions subsequently or simultaneously.

In the present embodiment, the insert 6 is preferably moveable radially and/or outwardly and/or away from the airpump 18 and/or in its longitudinal direction and/or in the main discharge direction and/or in the main extension of the mouthpiece 24. However, other movements are also possible. In the present case, only a translational movement is provided. However, a rotational or pivotal movement can be provided additionally or alternatively or superposed.

Preferably, the storage device 4, the carrier 5 and/or the cavities 7 comprise means for limiting the possible or maximum movement of the inserts 6. Preferably, this means stops the insert(s) 6 by form-fit. In the present embodiment, the means comprise stops 22, e.g., shoulders, protrusions or the like, which interact with a respective abutment, such as a shoulder 23, of the respective insert 6 so that the insert 6 is limited in its movement out of the respective cavity 7, as shown schematically in FIG. 4, where the shoulder 23 abuts the respective stop 22, and thus, prohibits any further outward movement of the insert 6. However, it is noted that any other technical solution having the same effect can also be used.

For dispensing, the gas (air) is supplied under pressure to the storage chamber 10 via the piercing element 17 or any other suitable connecting or supply element.

The gas (air) generates a respective flow in the storage chamber 10 to mix gas and powder and to force the dose through the duct 12.

FIG. 5a shows a preferred construction or design of the dispensing device 1. In this embodiment, the means for pressurizing gas (air pump 18) comprises the bellows 27 for pressurizing gas, in particular, air. The bellows 27 may be actuated by a spring means, in particular, a spring 28, as schematically shown. In particular, the spring means compresses the bellows 27 during the dispensing operation to pressurize the gas and to supply the gas to the connected storage device 4/storage member/insert 6/storage chamber 10 via the connecting or supply mechanism 20/connecting element/piercing element 17. Thus, a gas stream is generated, as shown by arrows 40, during the dispensing operation. The gas stream 40 flows through the storage device 4/storage chamber 10, entrains the respective dose of the formulation 2 and is ejected via the duct 12 to generate the spray 3, as schematically shown in FIG. 5a. However, other constructions, in particular, of the means for pressurizing gas, are possible.

Preferably, the dispensing device 1 or storage device 4 or means for pressurizing gas comprises a throttle for throttling the gas stream 40. In the present embodiment, the throttle is formed by a restriction and/or the connecting element, i.e., here by the hollow needle or piercing element 17. However, other constructional solutions are possible.

Preferably, the throttle is located stream up, in particular, just before, the storage chamber 10. However, it is also possible to form the throttle within the storage chamber 10 or downstream thereof, in particular in or by the duct 12 or the like. In one embodiment (not shown), the throttle may be formed at or by the transition portion 45 or the entry opening 46 of the duct 12.

Figure 5B:
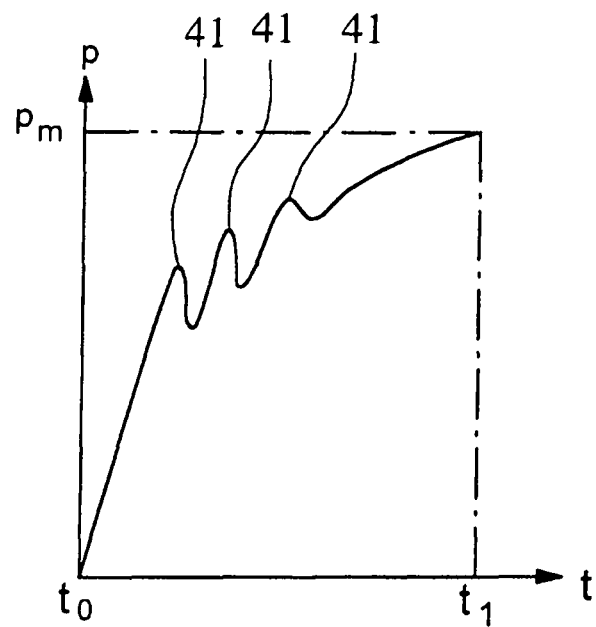

According to one aspect of the present invention, the dispensing device 1 is designed such that pressure pulses 41 are generated in the gas stream 40 during dispensing one dose of the formulation 2 as shown in an exemplary manner in the schematic pressure diagram or curve according to FIG. 5b.

FIG. 5b is a very schematic diagram. The curve shows the pressure p over the time t. The pressure curve p shows in an exemplary manner that pressure pulses 41 occur during the dispensing operation or period, here from time $t_0$ to $t_1$.

The pressure p approaches during the period of dispensing a maximum pressure $p_m$ as schematically shown in FIG. 5b. However, this behavior may vary very strongly depending on the dispensing device 1, storage device 4 and the like.

According to the preferred embodiment, the pressure pulses 41 are generated by a respective resonance system, preferably formed between and/or by the throttle and/or air pressurizing means.

Alternatively or additionally, the pressure pulses 41 can be generated by means of a valve or the like in the gas supply, e.g., by means of valve 44 mentioned later.

Preferably, the bellows 27 and/or spring means, such as the spring 28, oscillate or vibrate during the dispensing operation caused by the pressure pulses 41 or causing the pressure pulses 41.

Figure 5C:
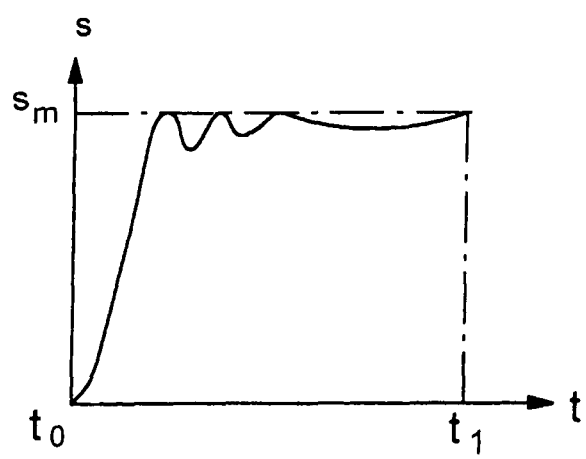

The schematic diagram of FIG. 5c shows the stroke or amplitude or compression of the bellows 27, of a pump piston or of the spring 28 over the time t. It can be seen from the curve that the stroke relatively quickly increases to its maximum stroke $s_m$, and then, oscillates during the period of dispensing from $t_0$ to $t_1$ resulting in the pressure pulses 41.

Preferably, 2 to 5 pressure pulses 41 are generated during each dispensing operation.

The pressure pulses 41 preferably comprise a decrease of the gas pressure by at least 300 kPa/s, in particular at least 500 kPa/s or more. These pressure drops or decreases occur during the dispensing operation, i.e., when the gas stream 40 flows through the storage device 4. In particular, this pressure decrease does not relate to the pressure drop at the end of the dispensing process.

The pressure pulses 41, and in particular, the associated variations of the flow rate of the gas stream 40 can loosen the formulation 2.

Further, the pressure pulses 41 can generate or result in higher shear forces so that de-agglomeration of the formulation 2 is enhanced.

Additionally or alternatively, the pressure pulses 41 may prohibit any clogging of small openings, chambers, channels or the like, in particular of the duct 12.

According to a further aspect of the present invention, which aspect can be realized alternatively or additionally, the direction of gas flow, i.e., of the gas stream 40, alternates, preferably at least once, in particular, at least 2 to 5 times, during a dispensing operation or process. This change of the flow direction results in the same or similar advantages as described above with respect to the pressure pulses 41. In particular, the alternation of the flow direction can be caused by the pressure pulses 41 and/or by a respective oscillation of a piston, of the bellows 27 or the like of the means for pressurizing gas. However, other constructional solutions are possible as well.

Preferably, the flow direction of the gas stream 40 is reversed only for a very short period with respect to the total period of the dispensing operation or process. In particular, the short period of reversing the flow direction is at most 5%, in particular about 2% or less, of the total period of the inhalation operation or process.

The powder will be discharged—in particular, forced through the duct 12—with a comparatively low gas pressure (preferably less than 300 kPa, in particular, about 50 kPa to 200 kPa). This low gas pressure, which is significantly lower than the gas pressures in the prior dispensing devices, enables a respectively low discharge velocity, and therefore, a slow spray 3 with slow propagation velocity.

Preferably, the storage chamber 10 forms a mixing chamber for mixing the gas with the powder. The chamber 10 is preferably designed such that the gas can generate swirls or eddies for better mixing the powder with the gas. Preferably, the chamber 10 is substantially circular in cross section, in particular cylindrical. However, other shapes are also possible.

Further, the chamber 10 is formed with no sharp edges, corners or the like, but has a smooth contour so that the gas can sweep all chamber surfaces to prevent powder accumulating on them and to ensure or allow complete discharge of the powder. In particular, the gas inlet formed by the piercing element 17 or any other supply element is located opposite to the outlet, i.e., duct 12 and/or nozzle 13, with regard to the axial or outlet direction.

During the dispensing operation, the spray 3 is preferably directly or only generated by the respective insert 6 or its duct 12 and output into a mouthpiece 24 of the dispensing device 1 as shown in FIGS. 1 & 5 for inhalation by a patient or user.

After dispensing one dose, or before or for dispensing the next dose, the piercing element 17 will be withdrawn from the connected insert 6. Preferably, the respective insert 6 is also retracted or pushed back into its cavity 7.

Then, the carrier 5 will be indexed one step further or to the next insert 6, in particular, rotated by means of an indexing or transport mechanism (not shown). This mechanism is preferably operated by actuating actuator 19 or any other actuator, by opening a cap or cover of the dispensing device 1 or the like, as already mentioned.

It is noted that the present invention, in particular, the dispensing device 1 and/or the storage device 4, can be used for dispensing one drug, a blend of drugs or at least two or three separate drugs. In the latter case, the separate drugs are stored in separate storage chambers 10, and during the dispensing operation, the drugs are mixed with the gas, either in a common mixing chamber or in their respective storage chambers 10. Further, the separate drugs can be discharged through a common duct 12 or through separate ducts 12. In the latter case, the separate drugs will be mixed after leaving the separate ducts 12 or in the mouthpiece 24 or in any other suitable (additional) mixing chamber. It is also possible to mix the separate drugs by impinging jets of the separate drugs. For dispensing the separate drugs, it is preferred to use a common gas supply or means for pressurizing gas such as air pump 18.

Preferably, the spray 3 has a mean velocity (taken 20 cm from the outlet 15 or mouthpiece 24) of less than 2 m/s, in particular, less than 1 m/s. Preferably, the mean duration of the spray 3 is at least 0.2 or 0.3 s, in particular, about 0.5 to 2 s.

In the preferred embodiment according to FIG. 1, the cavities 7 are orientated in tangential or radial direction of the storage device 4 or carrier 5. Consequently, the inserts 6 can be individually moved in tangential or radial directions, in particular, outwardly, in order to open the respective outer seal 9 for dispensing the respective dose of the formulation 2 as indicated in FIG. 1. Accordingly, the mechanism 20 preferably operates in a radial direction for connecting the inserts 6 individually to a gas supply and for pushing the inserts 6 individually at least partially out of the respective cavity 7 and/or through the respective seal 9. This radial movement allows a very compact design of the dispensing device 1, in particular, in the axial direction.

Preferably, the mouthpiece 24 and the dispensing direction extend in a radial or tangential direction, as shown in FIG. 1.

Preferably, the dispensing device 1 comprises a lever or handle (not shown) or the actuator 19 or any other driving or actuation means for preferably manual actuation in order to index the carrier 5 one step further, i.e., to the next insert 6, and/or to operate the mechanism 20, preferably to connect the respective insert 6 to the gas supply and/or to move/push the respective insert 6 and/or to open the respective seal 9 for dispensing the respective dose of the formulation 2.

It is noted that the dispensing device 1 operates preferably only mechanically.

According to another embodiment (not shown), the inserts 6 may be formed as capsules, blister pockets or the like without any duct 12, or the like. Instead, each insert 6 is connected individually to a gas supply and to a common outlet arrangement, such as a duct 12, nozzle or the like for dispensing the respective dose of the formulation 2.

According to another embodiment, a secondary packaging may be used for packing and protecting the storage device 4/carrier 5, in particular for storage purposes, before inserting the storage device 4/carrier 5 into the dispensing device 1. Additionally, the whole device 1, including the storage device 4/carrier 5, may be stored in a secondary water vapor proof packaging.

Figure 6:
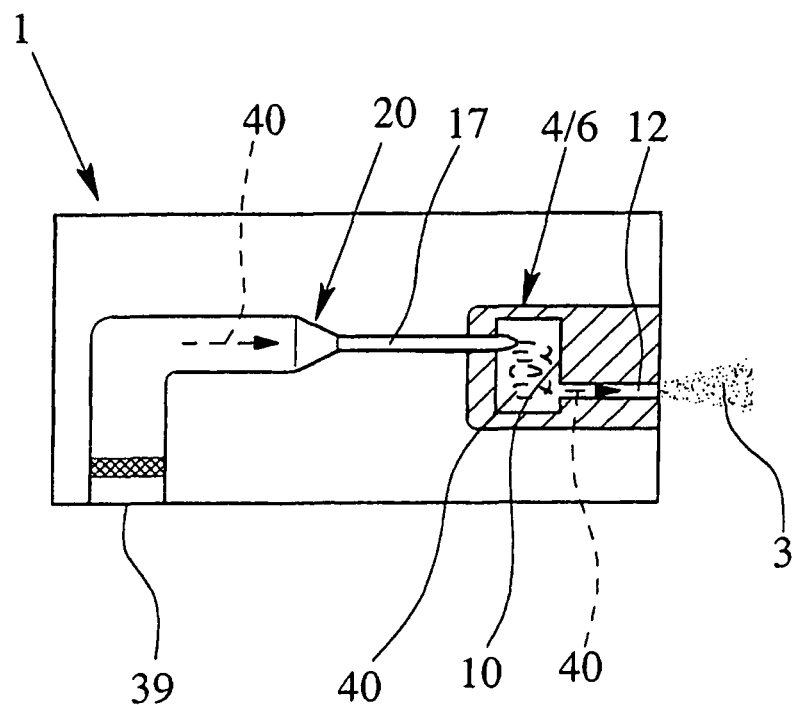

According to another embodiment shown schematically in FIG. 6, the dispensing device 1 may also be a passive inhaler wherein a patient or user (not shown) forces sucks an air flow through the respectively opened insert 6, when breathing in so that this airflow entrains the formulation 2 and forms the desired spray 3 in the mouthpiece 24 for inhalation by the patient/user.

In particular, the dispensing device 1 comprises an air inlet 39 through which the air can enter. The air inlet 39 is fluidically connected to the connecting/supply means 20 and the connecting element/piercing element 17 so that the air sucked in can form the gas stream 40 which flows through the storage device 4/storage chamber 10 and dispenses the formulation 2 as spray 3 in the desired manner.

According to a further embodiment, the dispensing devise 1 may be breath activated, in particular, wherein the formulation 2 is only released after the patient's or user's inhalation rate has reached a predetermined level, preferably by the use of a pressure sensitive means, such as a bursting element, membrane or valve, or any other mechanism.

It is noted that the term "dispensing device" has to be understood in a broad sense to include other discharge devices, dispensers or the like, preferably wherein the formulation 2 or any other fluid is sprayed or atomized only when needed, in particularly discontinuously.

In the following, a further preferred embodiment of the dispensing device 1 will be explained with reference to the further drawings. The following description will focus on relevant differences between the further embodiment and the previous embodiments. In particular, the previous explanations and descriptions apply accordingly and/or additionally, even if not repeated.

FIG. 7 shows the further embodiment of the dispensing device 1 in a perspective view. The dispensing device 1 comprises a cover 25 for covering the mouthpiece 24. Preferably, the cover 25 can be pivoted to open or uncover the mouthpiece 24 as shown. Preferably, the mouthpiece 24 is snapped to a housing 26 of the dispensing device 1.

The dispensing device 1 comprises the actuator 19 at one side of its housing 26, preferably on the opposite side of the mouthpiece 24 and/or opposite to the main spray direction (preferably in a radial direction) of the dispensing device 1. The actuator 19 forms preferably a grip or handle. Therefore, the term "grip" will be used in the following.

The grip 19 is preferably moveable in a radial direction for actuating the dispensing device 1 as explained later in more detail. In particular, the grip 19 can be pulled radially outwardly from the initial position shown in FIG. 7 and pushed back into its initial position. These operations may be named "pulling" and "pushing", respectively, in the following. However, it is noted that these operational movements could also be realized by any other direction or type of movement, such as a non-translational movement.

First of all, the basic principle of the dispensing device 1 will be explained with reference to FIGS. 8 to 10. FIGS. 8 to 10 show only very rudimentary schematic views (not to scale) of inner components of the dispensing device 1 for explaining the principle. In particular, the housing 26 and the grip 19 have been omitted. Further, the storage device 4 is shown only in a schematic manner, in particular, incompletely or partially only in FIGS. 9 & 10. In particular, multiple details, such as seals 9, outlets 15 or the like, have been omitted. The preferred construction of the storage device 4 will be explained later after explaining the basic functional principle of the present dispensing device 1.

The dispensing device 1 is an active atomizer or inhaler. The means for pressurizing gas is preferably also constructed as air pump 18. Here, the air pump 18 comprises the bellows 27 as pumping element. However, any other suitable pumping element, such as a piston, could be used.

The dispensing device 1/air pump 18 further comprises an energy or spring store, in particular, the spring 28, for actuating the pumping element, i.e., the bellows 27.

The air pump 18 (bellows 27 and spring 28) is preferably radially moveable, in particular, in a sliding manner or like a sled. Preferably, the air pump 18 forms a slider 29 or is supported thereon. In particular, the air pump 18 and slider 29 will be called an "air assembly" in the following.

Preferably, the air assembly forms or includes the mechanism 20 already mentioned with respect to the previous embodiments. For this purpose, the air assembly preferably comprises a needle holder 30 holding the piercing element/needle 17. The piercing element 17 may be pressed and/or glued or molded into the needle holder 30. Preferably, the bellows 27 is pressed or clamped onto the needle holder 30.

The needle holder 30 may be designed such that it can push the respective inserts 6 outwardly in case the sleeve 21 or any other abutment fails.

The needle holder 4 preferably closes or completes the slider frame 31. For example, the needle holder 30 may comprise holds for pins of the slider frame 31, which pins may be heat-riveted.

The needle holder 30 is connected to or formed by a slider frame 31, which, in turn, holds the spring 28 and/or moveably guides a tension element 32 associated with the bellows 27 and/or spring 28.

In the embodiment shown, the bellows 27 is arranged between the needle holder 30 and the tension element 32. The spring 28 is arranged behind the bellows 27, e.g., on the opposite side of the tension element 32.

The tension element 32 holds the bellows 27 in order to secure the filling of the bellows 27 during pulling. Namely, the grip 19 preferably retracts the tension element 32 during pulling.

The air pump 18 or air assembly is preferably located in the center of the dispensing device 1 and/or within the storage device 4 and/or ring-like carrier 5 and/or is preferably radially moveable.

Figure 8:
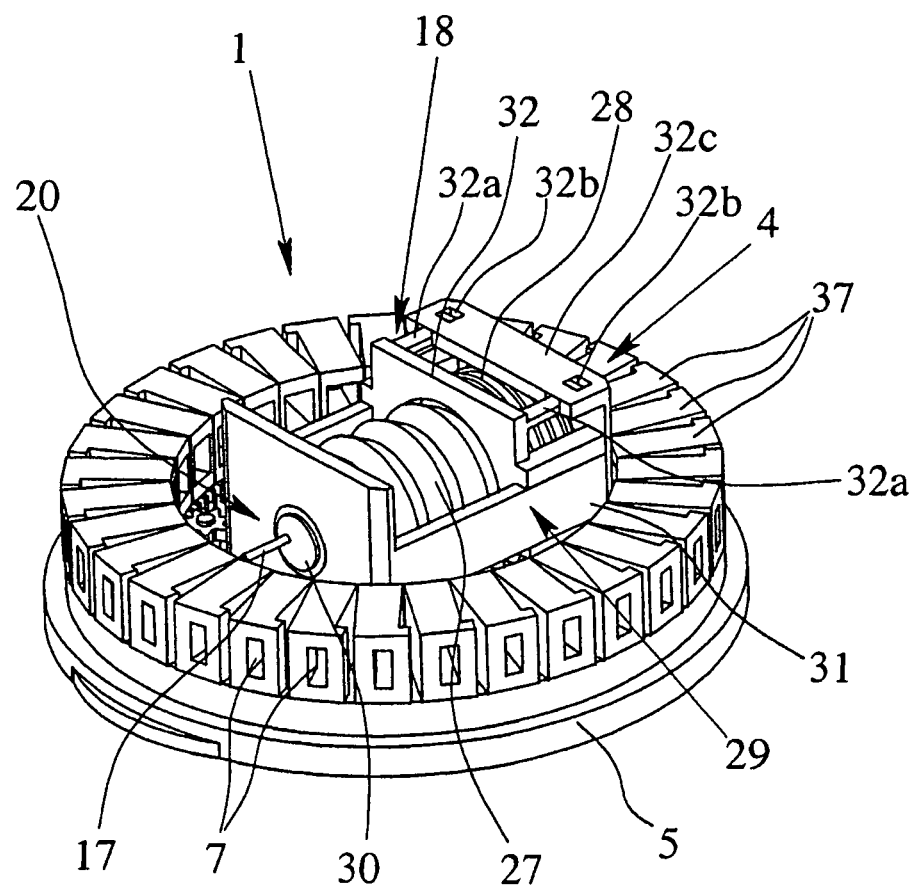

FIG. 8 shows the situation after the grip 19 (not shown) has been pulled out. The bellows 27 is extended and filled with air. The spring 28 is compressed or tensioned, i.e., the energy store has stored energy. The tension element 32 is retracted and locked in its position to hold the spring 28 in its compressed state. The air assembly/slider 29 is retracted so that the piercing element 27 is retracted from the storage device 4, in particular, so that the storage device 4 can be indexed or moved, in particular rotated.

When the grip 19 is pushed back, preferably a transportation operation and a connecting operation will be performed.

*In the first phase of the movement of the grip 19, a transport mechanism 33 is actuated. In particular a cogwheel 34 of the transport mechanism 33 (shown in FIG. 9) at least temporarily meshing with a preferably inner teeth 35 of the storage device 4 or carrier 5 is rotated to move or index the storage device 4 by one insert 6 or cavity 7 and/or to the next insert 6 or cavity 7. However, it is noted that this transportation operation could also be performed partly or completely during pulling.

Figure 9:
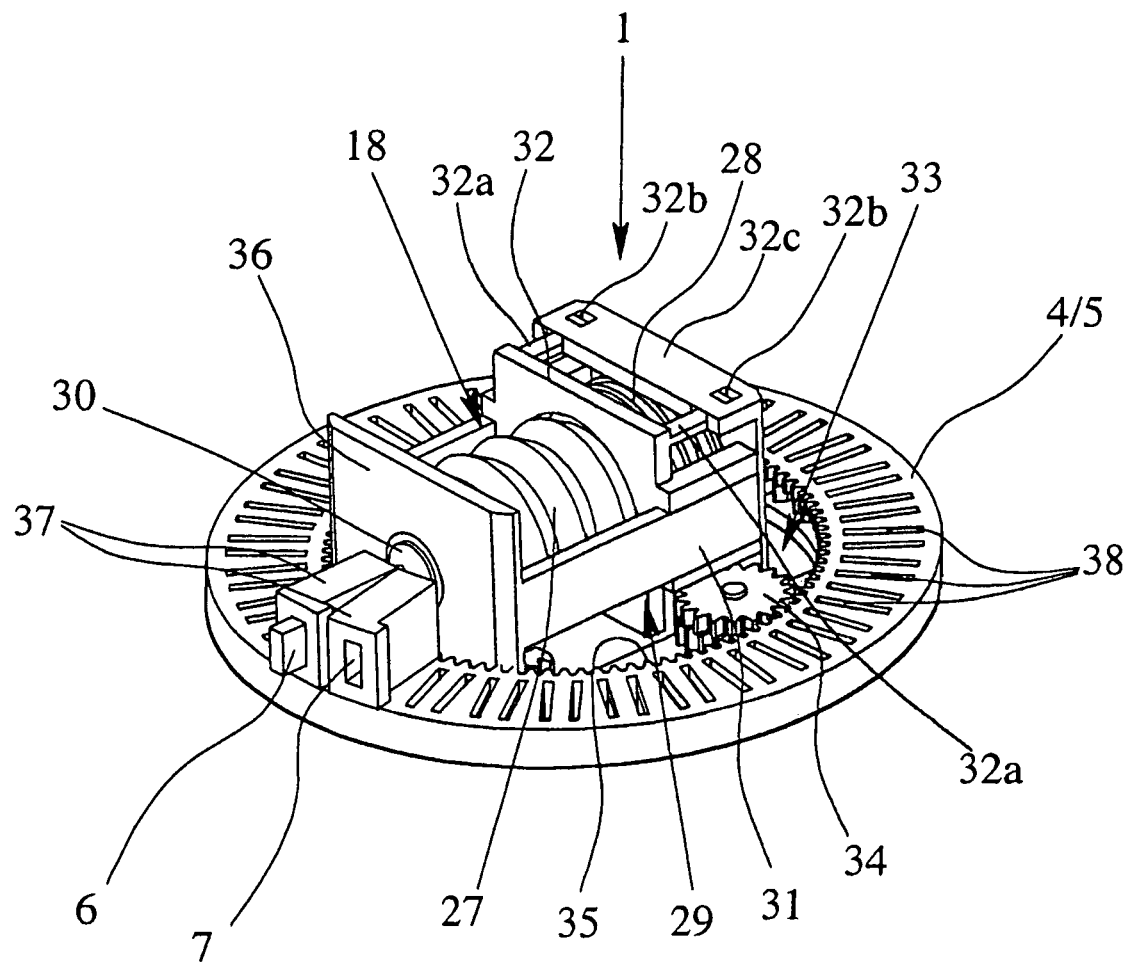

Preferably after termination of the transportation operation, i.e., during a second phase of pushing, the connecting operation is performed. The air assembly/slider 29 is moved forward and/or radially so that the piercing element 17 connects to the next/aligned insert 6/cavity 7. In particular, the piercing element 17 pierces into the insert 6 to connect to its storage chamber 10. Before, simultaneously and/or subsequently, the insert 6 is moved radially and/or outward and/or pushed through the outer seal 9. Thus, the insert 6/duct 12/outlet 15 is opened. This situation is shown in FIG. 9, wherein the connected and opened insert 6 is protruding radially outwardly from the storage device 4 and/or its cavity 7.

The spring 28 is still biased or compressed. This situation is also named "activated state". The dispensing device 1 is ready for dispensing the dose of formulation 2 from the opened/protruding inserts 6 shown in FIG. 9.

Figure 7:
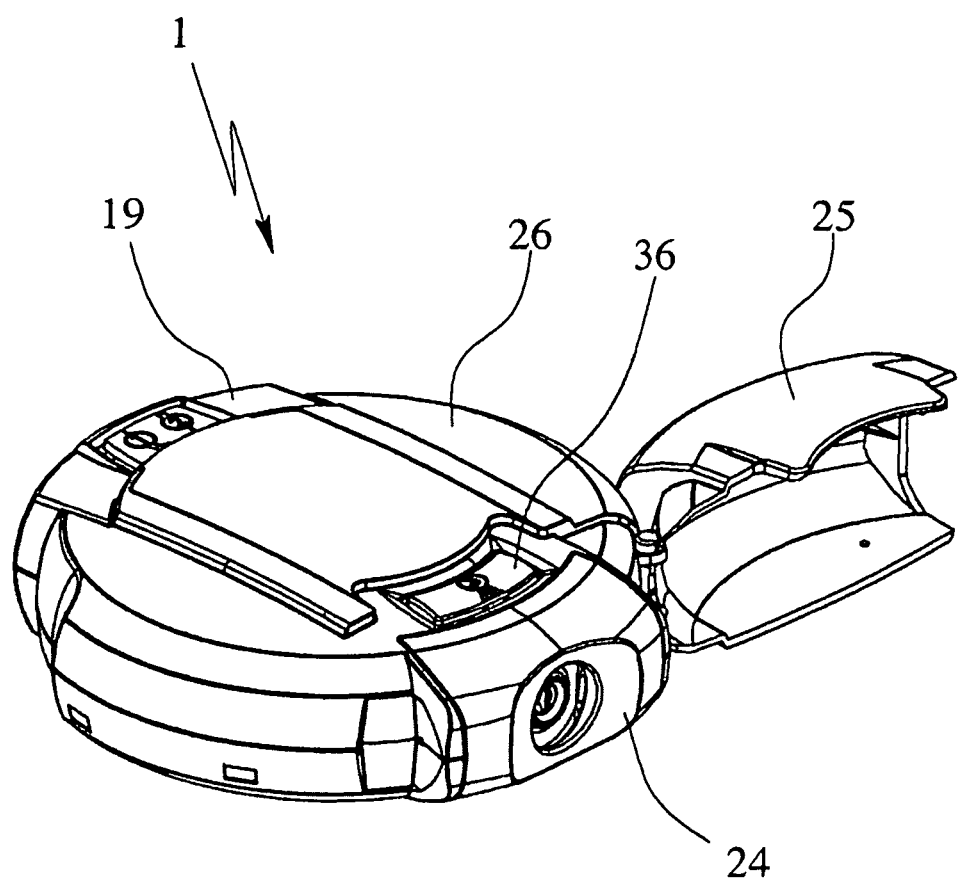

To initiate delivery (discharge) of the formulation 2 and to generate the spray 3, a release button 36 (shown in FIG. 7) or any other suitable element is actuated, in particular depressed. Thus, the tension element 32 or its associated locking means is unlocked (preferably by depressing/compressing the elastic snap arm 32a), and the spring 28 is released and compresses the bellows 27. The bellows 27 compresses the air contained therein. Thus, the air is pressed through piercing element 17 into the connected insert 6. The resulting air stream is forced through the connected insert 6, entrains the powder/formulation 2 of the insert 6 and ejects as spray 3 (not shown).

Figure 10:
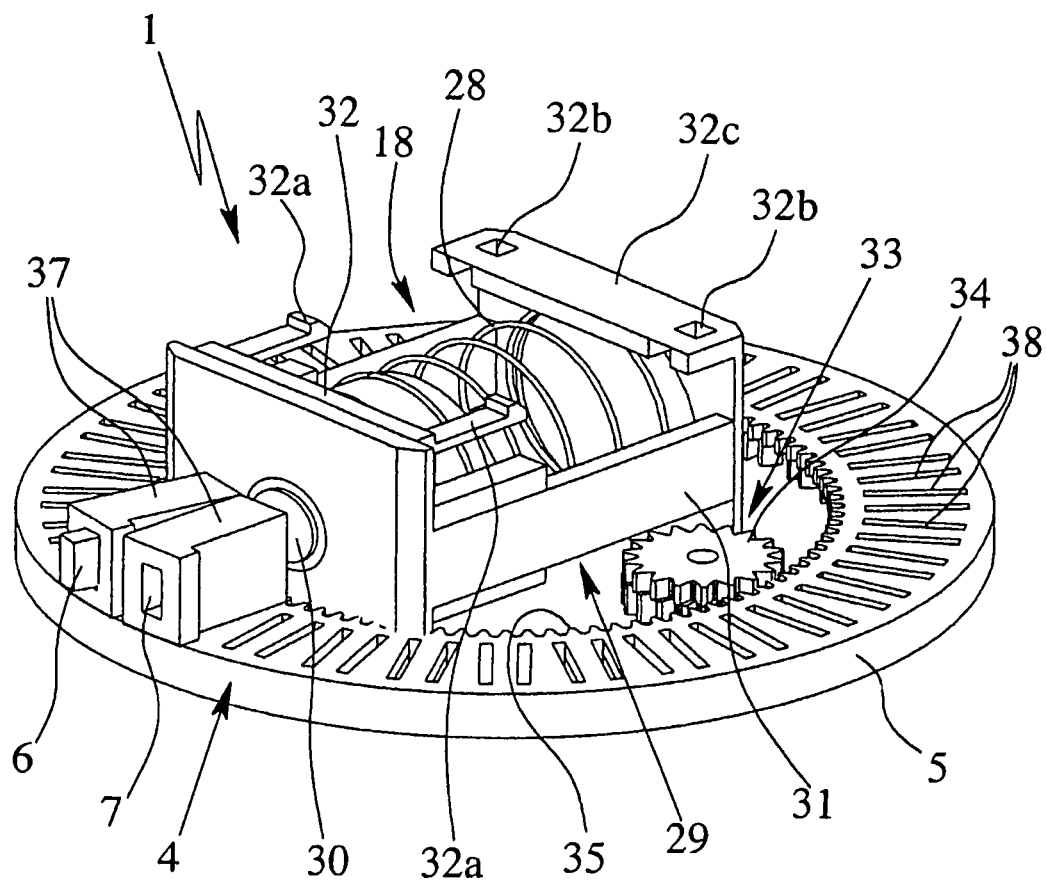

FIG. 10 shows the final state after discharge. The spring 28 is expanded. The bellows 27 is compressed. The tension element 32 has been moved forward to the needle holder 30/piercing element 17. The piercing element 17 is still connected to the emptied insert 6, and the emptied insert 6 is still protruding outward. In this state, the dispensing device 1 can be closed and transported. Therefore, this state is also named "transportation state".

For the next use, the grip 19 is pulled. In a first phase of the movement, the slider 29/air assembly is retracted together with the piercing element 17 so that the piercing element 17 is retracted from the storage device 4, i.e., out of the cavity 7 of the last insert 6. In a second phase of movement, which can also happen simultaneously, but is preferably performed after stop of the slider 29, the tension element 32 is retracted within the slider 29/slider frame 31 so that the bellows 27 is extended and the spring 28 is compressed or biased until the tension element 32 is locked in its retracted position as shown in FIG. 8. During the extension of the bellows 27, air is sucked into the bellows 27, preferably through piercing element 17 and/or optionally through a suitable inlet valve (not shown).

It is noted that the release button 36 is preferably lifted only during the last phase of pushing the grip 19. Further, the lifted or activated or primed release button 36 preferably blocks pulling of the grip 19 until the release button 36 has been actuated or depressed, i.e., until the dispensing device 1 has been triggered. In particular, the release button 36 is tilted during actuation or depressing.

In the following, further details, aspects, features and advantages of the present dispensing device 1 and/or of its components will be explained.

Preferably, the storage device 4 comprises multiple receptacles 37 respectively containing only or at least one insert 6, as schematically shown in FIG. 8 to 10. In particular, the receptacles 37 are produced as separate parts that are placed or mounted on the carrier 5.

Preferably, the receptacles 37 are engaged in or held by recesses 38 on the carrier 5.

The receptacles 37 may be made of the same material as the storage device 4/carrier 5, in particular of plastic. Preferably, the receptacles 37 are rigid and form a guide for the inserts 6.

Each receptacles 37 comprises only one or multiple cavities 7 for receiving the respective insert(s) 6.

Preferably, the receptacles 37 are provided with the inserts 6 already filled with the respective dose of formulation 2 and, then, mounted on the comment carrier 5.

The receptacles 37 are preferably sealed separately, i.e., independently from each other and/or with separate seals 9. The receptacles 37 may be sealed before or after placement on the carrier 5.

The receptacles 37 are preferably sealed on opposite sides and/or on longitudinal end faces.

Preferably, the receptacle 37 has an essentially cuboid and/or longitudinal form.

The carrier 5 preferably supports the receptacles 37 fixedly and/or in a form-fit manner. Preferably, the receptacles 37 are snapped on to or into the carrier 5.

Preferably, the air assembly/slider 29 and the storage device 4/carrier 5/receptacles 37 interact such that a correct alignment of the piercing element 17 and the respective receptacle 37 or insert 6 is ensured before the piercing element 17 pierces or opens the respective receptacle 37, cavity 7 and/or insert 6.

Preferably, the inserts 6 are restricted in their backward movement as already mentioned so that the piercing element 17 can be retracted and uncoupled from the respective insert in a definitive manner when the air assembly/slider 29 is retracted into the position shown in FIG. 8.

In the present embodiment, a locking means is provided for locking the tension element 32 in the retracted position. Here, the locking means comprises at least one snap hook or arm 32a, preferably two or more snap arms 32a engaging into respective undercuts, recesses or snap openings 32b preferably formed by or in a back shield 32c of the slider 29 or slider frame 31 or vice versa. However, other constructional solutions are possible.

The dispensing device 1 is preferably an active powder inhaler, i.e., the powder is discharged by pressurized gas, in particular air. Nevertheless, the dispensing operation may be triggered by the inhalation or breathing in of a patient (not shown). In particular, the dispensing device 1 may comprise detection means for detecting inhalation or breathing in and/or trigger means for triggering dispensing of the respective dose.

Preferably, the detection means comprises a sensor 42 for detecting at least one of a pressure, a pressure drop, a velocity, an increase of velocity or any associated value thereof regarding the air flowing through the dispensing device, in particular the mouthpiece 24, when a patient breathes in.

The respective detection signal indicating breathing in of a patient may be used by the trigger means in order to trigger dispensing of the respective dose by means of pressurized gas. In particular, the trigger means comprises a controller 43 and/or a valve 44 associated to the means for pressurizing gas, in particular the air pump 18, a gas supply line, the piercing element 17 or the like so that start of flow of pressurized gas to and through the respective storage chamber 10 or the like for dispensing the respective dose of formulation 2 may be controlled or triggered.

Preferably, the trigger means operate electrically or electronically or pneumatically or mechanically. For example, the detection means and trigger means may be formed only by an appropriate valve 44 that opens the supply of pressurized gas through the respective receptacle 37, insert 6 and/or storage chamber 10 when the pressure in the mouthpiece 24 drops due to breathing in of a patient. Then, the valve 44 preferably stays open until the flow of pressurized gas stops or the gas pressure reaches or drops bellow an appropriate pressure limit. Such a functionality may be realized without using electric or electronic components.

There are multiple other mechanism possible. According to another embodiment, a sealed outer case can have a flexible diaphragm, e.g., made of rubber, mounted within its wall with one surface facing the inside and the other exposed to atmosphere. A linkage with mechanical advantage (amplification) connects the diaphragm to the tension element 32 (FIGS. 8 and 9) or to the valve 44 or any other suitable means to control gas supply. When the user or patient inhales via the mouthpiece 24 the sealed case ensures a pressure reduction due to which bents the diaphragm into the case activating or acting on the mechanical link and, thus, triggers dispensing, in particular by releasing tension element 32, opening valve 44 or the like.

According to another embodiment, a flap can be seally positioned within the mouthpiece 24 and connected to the tension element 32, the valve 44 or the like via a linkage with mechanical advantage or amplification. When the user or patient inhales, the air flow/pressure difference opens or actuates the flap activating or operating the link and, thus, triggering dispensing, in particular by releasing tension element 32, opening valve 44 or the like.

According to another embodiment, an electronic system can be used. A pressure sensitive actuator can be connected to tension element 32 so that tension element 32 can be released when detecting inhalation or breathing in of a user or patient.

Preferably, the automatic triggering or dispensing is only possible when the dispensing device 1 has been activated and/or dispensing has been allowed, in particular by actuating the release button 36 or any other actuator, before the trigger means may eventually trigger the dispensing when breathing in is detected.

In case of the present preferred ring arrangement, the indexing direction extends in the tangential and/or circumferential direction. The term "indexing direction" means preferably the direction in which the storage device 4 is moved, in particular rotated, stepwise from one receptacle 37, cavity 7 or insert 6 to the next one so that the respective doses of formulation 2 can be discharged one after the other.

In particular, the dispensing device 1 is a preferably oral and/or active inhaler, a hand-held device and/or preferably only manually operated. Most preferably, the dispensing device 1 is a dry powder inhaler.

Individual features and aspects of the different embodiments may also be combined with one another as desired or used in other constructions of atomizers, inhalers, dispensers or the like.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and
3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one
4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}4H-benzo[1,4]oxazin-3-one
8-{2-[1,1-dimethyl-2-(2.4.6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2.6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

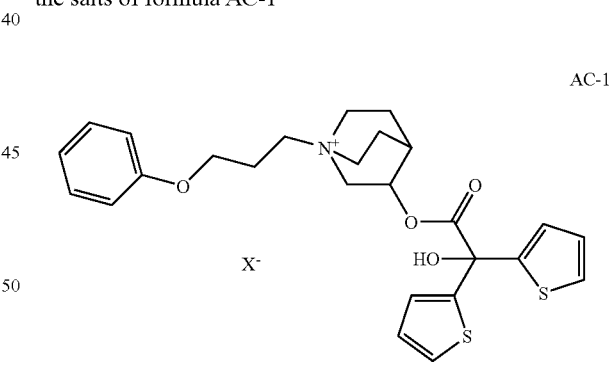

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

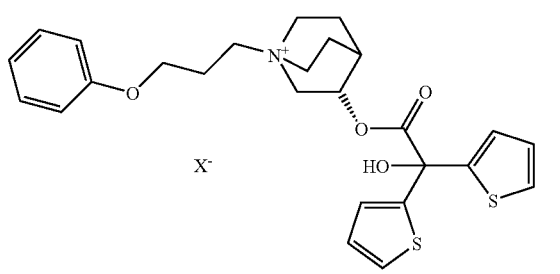

AC-1-en wherein X⁻ may have the above-mentioned meanings. Other preferred anticholinergics are selected from the salts of formula AC-2

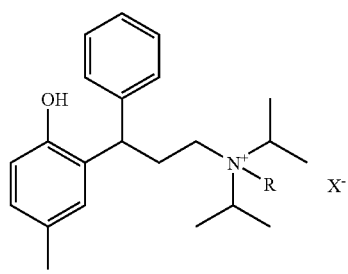

AC-2 wherein R denotes either methyl or ethyl and wherein X⁻ may have the above-mentioned meanings. In an alternative embodiment the compound of formula AC-2 may also be present in the form of the free base AC-2-base.

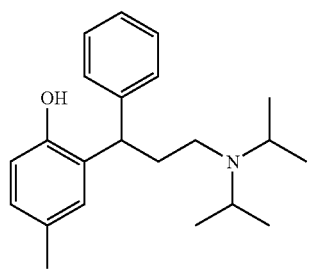

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide,
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3 S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example, sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-di fluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3.4-c]-1,2,4-triazolo[4.3-a]pyridine 9-cyclopentyl-5,6-dihydro-7-ethyl-3-(tert-butyl)-9H-pyrazolo[3.4-c]-1,2,4-triazolo[4.3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example, sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxyquinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl) amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methane-sulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonyl-methyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethane-sulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1'-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxy-ethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N—[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]
7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in European Patent Application EP 1 003 478 A1 or Canadian Patent Application CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Dispensing device for dispensing a formulation, containing at least one powder, as a spray, the dispensing device comprising:
    a hand-holdable housing,
    a storage device with a plurality of storage chambers, each of which contains a separate pre-metered dose of said formulation,
    means for sequentially bringing each of said pre-metered doses of the formulation into a dispensing position, and
    means for providing a pulsed flow of air, having multiple pressure pulses, into each pre-metered dose of the formulation that is in said dispensing position so as to loosen or deagglomerate the formulation and for dispensing the dose as a spray with desired spray plume characteristics,
    wherein the means for providing a pulsed flow of air comprises a bellows or piston pump on which a spring acts in a compressive direction and a connecting element having a flow restrictor through which pressurized air is supplied from the bellows or piston pump individually to an inlet of a respective one of the storage chambers of the storage device containing the pre-metered doses of the formulation, the spring and the flow restrictor being constructed in a manner producing oscillation or vibration of the bellows or piston pump after an uninterrupted period of increasing dispensing pressure or stroke.

2. Dispensing device according to claim 1, wherein the dispensing device is a dry powder inhaler.

3. Dispensing device according to claim 1, wherein the means for producing a pulsed flow of air is adapted to cause the direction of gas flow to alternate within the connecting element during dispensing of one dose.

4. Dispensing device according to claim 1, wherein the flow restrictor comprises a throttle.

5. Dispensing device according to claim 1, wherein the flow restrictor comprises a valve.

6. Dispensing device according to claim 1, wherein the means for providing a pulsed flow produces said multiple pressure pulses prior to reaching a maximum delivery pressure.

7. Dispensing device according to claim 1, wherein the means for providing a pulsed flow produces said multiple pressure pulses by oscillating after reaching a maximum delivery stroke.

* * * * *